United States Patent [19]
Hayakawa et al.

[11] Patent Number: 5,211,059
[45] Date of Patent: May 18, 1993

[54] ACOUSTIC MICROSCOPE SYSTEM

[75] Inventors: Yasuo Hayakawa; Sakae Takeda; Tosio Nonaka; Katsumi Miyaki; Hiroshi Yamamoto; Kazuo Fujishima, all of Ibaraki, Japan

[73] Assignee: Hitachi Construction Machinery Co., Ltd., Tokyo, Japan

[21] Appl. No.: 800,117

[22] Filed: Nov. 29, 1991

[30] Foreign Application Priority Data

Nov. 29, 1990 [JP] Japan ................................. 2-331647
Nov. 29, 1990 [JP] Japan ................................. 2-331648
Jan. 31, 1991 [JP] Japan ................................. 3-032003

[51] Int. Cl.$^5$ .......................................... G01N 29/000
[52] U.S. Cl. .......................................... 73/606; 73/626
[58] Field of Search .................. 73/606, 642, 626, 628

[56] References Cited

U.S. PATENT DOCUMENTS

| | | | |
|---|---|---|---|
| 4,503,708 | 3/1985 | Kino et al. | 73/606 |
| 4,524,621 | 6/1985 | Yamanka | 73/606 |
| 4,541,281 | 9/1985 | Chubachi et al. | 73/606 |
| 4,655,083 | 4/1987 | Chubachi | 73/606 |

FOREIGN PATENT DOCUMENTS

| | | | |
|---|---|---|---|
| 0121890 | 4/1984 | European Pat. Off. | |
| 252554 | 11/1991 | Japan | 73/661 |
| 2221303 | 1/1990 | United Kingdom | 73/626 |

OTHER PUBLICATIONS

Electronic Letters, vol. 19, No. 22, Oct. 27, 1983, London GB, pp. 906-908; M. Nkoonahad et al.: "Rayleigh wave suppression in reflection acoustic microscopy". IEEE 1987 Ultrasonics Symposium, vol. 2, Oct. 16, 1987, Denver, Colo. USA, pp. 817-821; J. Kushibiki et al.; "Determination of elastic constants by LFB acoustic microscope".

Primary Examiner—Hezron E. Williams
Assistant Examiner—Nashmiya Ashraf
Attorney, Agent, or Firm—Sughrue, Mion, Zinn, Macpeak & Seas

[57] ABSTRACT

The present invention relates to an acoustic microscope system having an ultrasonic probe that is driven with a high-frequency burst signal to radiate an ultrasonic signal and that detects the resulting reflected and irradiated waves, a Z-axis moving device that updates the vertical distance Z between the probe and a material of interest for each sampling position, and device for constructing a V(z) curve from the reflection signals obtained at respective sampling positions. The ultrasonic probe of the invention is provided with an acoustic lens, a first ultrasonic transducer for receiving a leaky surface skimming compressional wave reflected from a sample material on one side of the acoustic lens, and a second ultrasonic transducer also provided on the side of the acoustic lens for receiving a leaky surface acoustic wave.

24 Claims, 11 Drawing Sheets

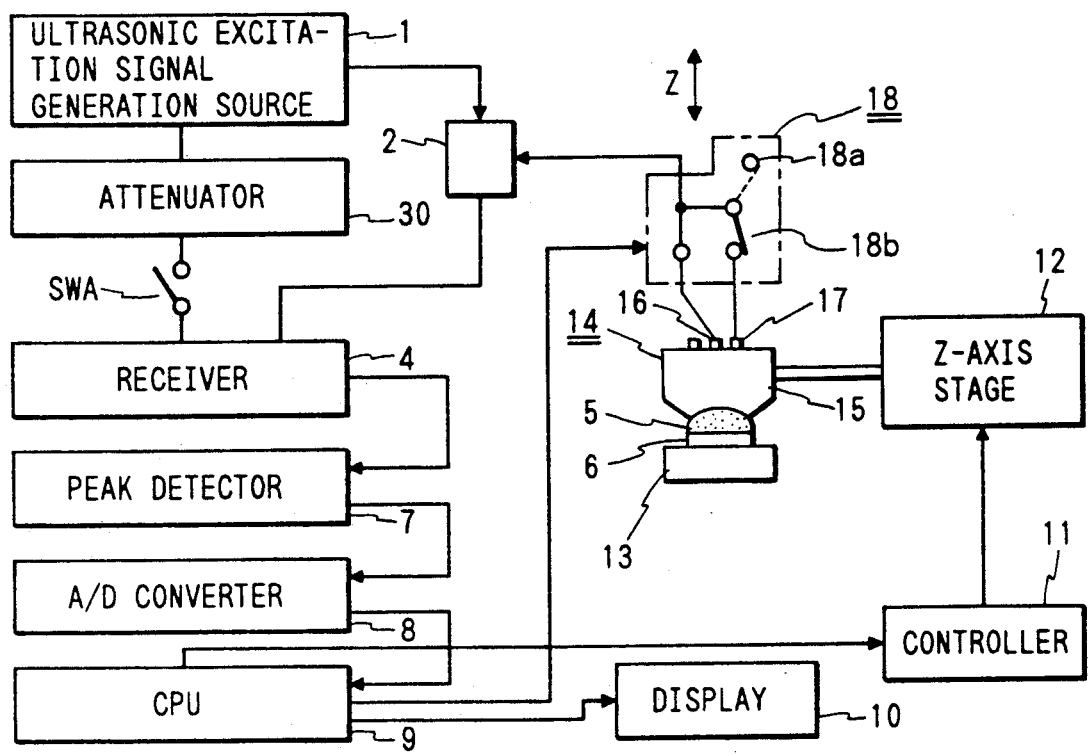

$W_A$ $W_C$

INTERFERENCE WAVE

INTERFERENCE WAVE
IN OPPOSITE PHASE

ACOUSTIC MICROSCOPE SYSTEM

BACKGROUND OF THE INVENTION

1. Field of the Invention

The present invention relates generally to an acoustic microscope system that can suitably be employed in measuring quantitatively the elastic characteristics of a testpiece using ultrasonic beams. More particularly, the invention relates to an improvement of an ultrasonic probe for use in the acoustic microscope system.

2. Related Art

An acoustic microscope system is an effective device in materials science for evaluating the characteristics such as the elastic characteristics of a particular material. For this purpose, the vertical distance (Z) between the material as a testpiece to be analyzed and an ultrasonic probe is varied while irradiating ultrasonic beams toward the testpiece to obtain the output voltage (V) of returning waves. As shown in FIG. 1, the output voltage (V) is a function of the distance Z and minimum values of the output voltage (V) of returning wave alternate with maximum values to provide a profile that is generally referred to as a "V(z) curve". The abscissa of this graph plots the distance Z ($\mu$m) and the ordinate plots the signal level (dB). The interval between adjacent maximum values (peaks) or minimum values (valleys) on the V(z) curve is called an "interference period $\Delta Z$", which is a very important parameter for evaluating materials of the testpiece. Since the interference period $\Delta Z$ depends upon the velocity of the Rayleigh wave or compressional wave returning from a testpiece while radiating ultrasonic beams toward the testpiece, it is first determined from the V(z) curve of that testpiece and the velocity of the Rayleigh wave or compressional wave is then determined from said $\Delta Z$.

The V(z) curve is a curve indicative of the periodical variation of the output voltage relative to the amount of defocus. The period $\Delta Z$ of the V(z) curve has a relation to the velocity $C_R$ of the Rayleigh wave and expressed by the following equation (1):

$$C_R = \frac{C_0}{\sqrt{1 - (1 - C_0/2f\Delta Z)^2}} \quad (1)$$

where $C_0$ represents the velocity of water and f represents a frequency of the incident ultrasonic wave.

On the basis of the foregoing equation, the elastic characteristics of a material can be expressed.

In order to obtain the V(z curve, an acoustic microscope apparatus employs an ultrasonic probe. There are two classes of ultrasonic probes so called as "point-focus-beam type probes" and "line-focus-beam type probes" as discussed below.

The ultrasonic probe is provided with an acoustic lens and a transducer mounted on an upper surface of the acoustic lens for irradiating ultrasonic beams toward a testpiece and receiving various types of waves reflecting from the testpiece. The transducer of the point-focus-beam probes consists generally of a circular-shaped piezoelectric element formed of ZnO, for example, and a pair of electrodes disposed an upper and lower surface of the piezoelectric element. The acoustic lens has at a lower surface thereof a spherical concave surface so that incident ultrasonic waves are focused at a point on an extending direction from the center of the spherical concave surface. Since all incident waves are focused at a single point, probes of this type are called as the point-focus type.

Probes of the point-focus type have two major advantages, that is, first, they can produce a C-scan image; second, they are capable of measuring the acoustic velocity of a surface wave in terms of the average for all directions in the points on the surface of the testpiece material to be analyzed.

FIG. 2 is a schematic view showing the conventional acoustic microscope system. A testpiece 6 placed on a table 13 is immersed in a couplant 5 such as water or the like, which is brought into contact with an ultrasonic probe 3. An ultrasonic excitation source 1 generates a high-frequency burst signal which is supplied to the probe 3 via a directional coupler 2. The probe 3 converts the input electric burst signal into ultrasonic waves which is focused by an acoustic lens of the probe 3 and radiated towards the testpiece 6 through the couplant 5.

The ultrasonic signal that has been reflected and scattered by the surface of the testpiece 6 is received by the same acoustic lens and reconverted into an electric signal, which is supplied to a receiver 4 via the directional coupler 2.

The electric signal supplied to the receiver 4 is amplified and thereafter sent to a peak detector 7 which detects peaks of the received signal. The detected peak value is read into a central processing unit (CPU) 9 via an A/D converter 8 and used as data for constructing a V(z) curve. Using this data, a display unit 10 indicates an appropriate image of the V(z) curve.

The ultrasonic excitation source 1 may be an impulse generator or a tone burst generator.

The system shown in FIG. 2 also includes a Z-axis stage 12 updating the vertical distance Z between the ultrasonic probe 3 and the testpiece 6 for each sampling position. The output of the probe 3 obtained at each sampling point can be expressed as a function of distance Z. The resulting expression is referred to as the V(z) curve. The Z-axis stage 12 is controlled to move up and down by means of a controller 11 which is controlled by commands supplied from the CPU 9.

An example of the condition of the reflected ultrasonic signal as detected by the probe 3 as well as waveforms thereof are described below with reference to FIGS. 3A to 3E.

FIG. 3A is an enlarged sectional diagram of the probe 3 showing the radiation and reflection of ultrasonic waves as they relate to the probe 3. The probe 3 consists of an acoustic lens 3a and a circular-shaped ultrasonic transducer 3b. The ultrasonic transducer 3b is composed of a piezoelectric device and a pair of upper and lower electrodes disposed on both top and bottom surfaces, respectively, of the piezoelectric device. A lead wire 3c connects to both the upper and lower electrodes for connecting to an external circuit.

It is recognized that the returning ultrasonic wave includes two components, one being a vertical reflection wave $W_D$ which is reflected directly and vertically from the testpiece 6 and the other being the transversal Rayleigh wave (leaky surface acoustic wave) $W_R$ which irradiates from the surface of the testpiece 6 substantially within the incident Rayleigh angle $\theta_r$. These two components interfere with each other and the result is received and detected as a reflection ultrasonic signal by the ultrasonic transducer 3b. The waveform of the vertical reflection wave $W_D$ is shown in FIG. 3B and the irradiated leaky surface acoustic wave (Rayleigh wave) $W_R$ in FIG. 3C. The wave of interference between in-phase components is shown in FIG. 3D and the wave of interference between 180° out-of-phase components is shown in FIG. 3E. The term 'interference' as used herein means the superposition of two wave components.

The peak values of the resulting interference wave are detected by the peak detector 7.

The V(z) curve for the peak values of the interference wave as a function of Z detected by the peak detector 7 is as illustrated in FIG. 1. Each of the maximum values (peaks) on the curve refers to the interference between in-phase wave components and each of the minimum values (valleys) refers to the interference between 180° out-of-phase components. Of course, there are various types of V(z) curves other than that shown in FIG. 1.

The V(z) curve and the associated ΔZ can be used to determine the acoustic velocities of the leaky surface acoustic wave, compressional wave, transversal wave, etc. with various materials of interest. Further, the elastic characteristics of the materials such as the differences in elastic modulus and density, Young's Modulus and, the differences in crystal size can be determined from the acoustic velocities of those waves.

Details of the conventional acoustic microscope system outlined above are given in journals such as "Kikai to Kogu (Machines and Tools)", November 1987, pp. 49-54, and "Zairyo (Materials)", December 1986, Vol. 35, No. 399, pp. 1-10.

The conventional line-focus-beam probes will now be described as follows with reference to FIGS. 4 and 5.

As shown in FIG. 4, an ultrasonic transducer 20 consisting of lower and upper electrodes 22, 24 and a piezoelectric element 23 is mounted on a flat top surface of an acoustic lens 21. The acoustic lens 21 has a cylindrical concave lens surface 21A on the side opposite to the side where the transducer 20 is mounted. A couplant (e.g. a water drop) 23 shown in FIG. 5 is provided between the concave lens surface 21A and a testpiece 26. The cylindrical concave lens surface 21A extends along a direction parallel to a longitudinal direction of the testpiece 26. FIG. 5 shows a cross section of the probe as taken in its longitudinal direction.

Focal point F shown in FIG. 5 is the point where an ultrasonic wave incident at the critical Rayleigh angle $\theta_r$ focuses in the water as the couplant 23, and a plurality of such focal points form a line directing along the longitudinal direction of the testpiece 26. Hence, the probe of this type is generally called as a line-focus-beam probe.

FIG. 5 refers to the case where an ultrasonic wave Wa irradiates from the concave lens surface 21A substantially within a critical Rayleigh angle $\theta_r$. The radiated ultrasonic wave travels on through the surface of the testpiece 26 as a leaky surface acoustic wave (Rayleigh wave) LSAW, which irradiates and returns back to the transducer 20 from the surface as an irradiated leaky surface acoustic wave Wb. An ultrasonic wave Wc that travels straight down through the acoustic lens 21 returns vertically to the transducer 20 as a vertical reflection wave Wd.

By measuring the irradiated and reflected waves Wb and Wd returning from the surface of the testpiece 26 with the vertical distance Z to the testpiece 26 being varied, a V(z) curve is constructed. The V(z) curve can be used to determine the sound velocity and other parameters to evaluate the various characteristics of the material of the testpiece 26.

The technique of the acoustic microscope employing the line-focus-beam type ultrasonic probe as described above is disclosed by Kushibiki et al. in "Evaluation of Substrates for Elastic Wave Devices" on pages 21-28 of the collected papers read at the 25th Symposium of Communications Research Institute of Tohoku University entitled "Ultrasonic Electronics—New Piezoelectric Applications", February 1989.

In order to determine the leaky elastic surface (Rayleigh) wave LSAW with the conventional system shown in FIGS. 1 to 5, the input ultrasonic wave must be radiated into the couplant substantially within the critical Rayleigh angle. In practice, however, the radiated wave contains partially the compressional wave component, that is, a leaky surface skimming compressional wave, which is difficult to detect as a separate entity after propagation through the surface of the testpiece because the signal level of the transversal leaky surface acoustic wave is much greater than that of the compressional wave component thereof. Thus, since the detected compressional wave is low in accuracy, it has been difficult to measure accurately the elastic characteristics of a material to be analyzed finally.

SUMMARY OF THE INVENTION

A primary object, therefore, of the present invention is to provide an acoustic microscope system capable of detecting a leaky surface skimming compressional wave to be measured separately from transversal leaky surface acoustic wave.

Another object of the present invention is to provide an ultrasonic probe for use in an acoustic microscope system which, whether it is of a line-focus-beam or point/focus-beam type, makes it possible to independently detect a leaky surface skimming compressional wave and a leaky surface acoustic wave both returning from a surface of a sample material and, further, accurately obtain the velocities of sound waves travelling through various anisotropic materials to be measured in a variety of modes.

The above and other objects can be achieved by the provision of an acoustic microscope system which, according to the invention, comprises an ultrasonic probe that is driven with a high-frequency burst signal to radiate an ultrasonic signal and that detects the resulting reflected and irradiated waves, a Z-axis moving means that updates the vertical distance Z between said probe and a testpiece of interest for each sampling position, and a means for constructing a V(z) curve from the signals returning from the sample material obtained at respective sampling positions. The ultrasonic probe of the invention is provided with an acoustic lens, a first ultrasonic transducer for receiving a leaky surface skimming compressional wave reflected from a sample material disposed on the acoustic lens, and a second ultrasonic transducer disposed on the acoustic lens for receiving an irradiated leaky surface acoustic wave (Rayleigh wave).

In one aspect of the present invention, the mode of driving the first and second ultrasonic transducers with high-frequency burst signals includes a first drive mode in which only the first ultrasonic transducer is actuated and a second drive mode in which both the first and second ultrasonic transducers are actuated simultaneously.

The acoustic microscope system of the present invention employs at least two ultrasonic transducers and, accordingly, this arrangement enables the leaky surface skimming compressional wave to be measured independently of the leaky surface acoustic wave.

Further, according to another aspect of the present invention, the objects of the invention can be attained by an ultrasonic probe for use in an acoustic microscope system is provided with an acoustic lens having a spherical or cylindrical concave lens surface and an ultrasonic transducer provided on one side of the acoustic lens, and the probe of the invention is characterized in that the transducer comprises a pair of circular and annular transducers or a plurality of transducers which are selectably actuated and arranged parallel to the longitudinal axis Of the concave lens surface and symmetric with respect to the central axis of the concave lens surface.

In case of the ultrasonic probe of the latter aspect of the present invention, the transducer is composed of a plurality of selectable transducers that are arranged to satisfy a certain relationship so that they can be selectively activated to permit selection of appropriate values of the critical Rayleigh angle and other parameters.

BRIEF DESCRIPTION OF THE DRAWINGS

FIG. 6A shows an acoustic microscope system according to the first embodiment of the present invention;

FIGS. 6B, 6C and 6D illustrate conditions of a switch 18 shown in FIG. 6A;

DESCRIPTION OF THE PREFERRED EMBODIMENTS

A first embodiment of the present invention will now be described in detail with reference to accompanying FIGS. 6–9.

Figure 2:
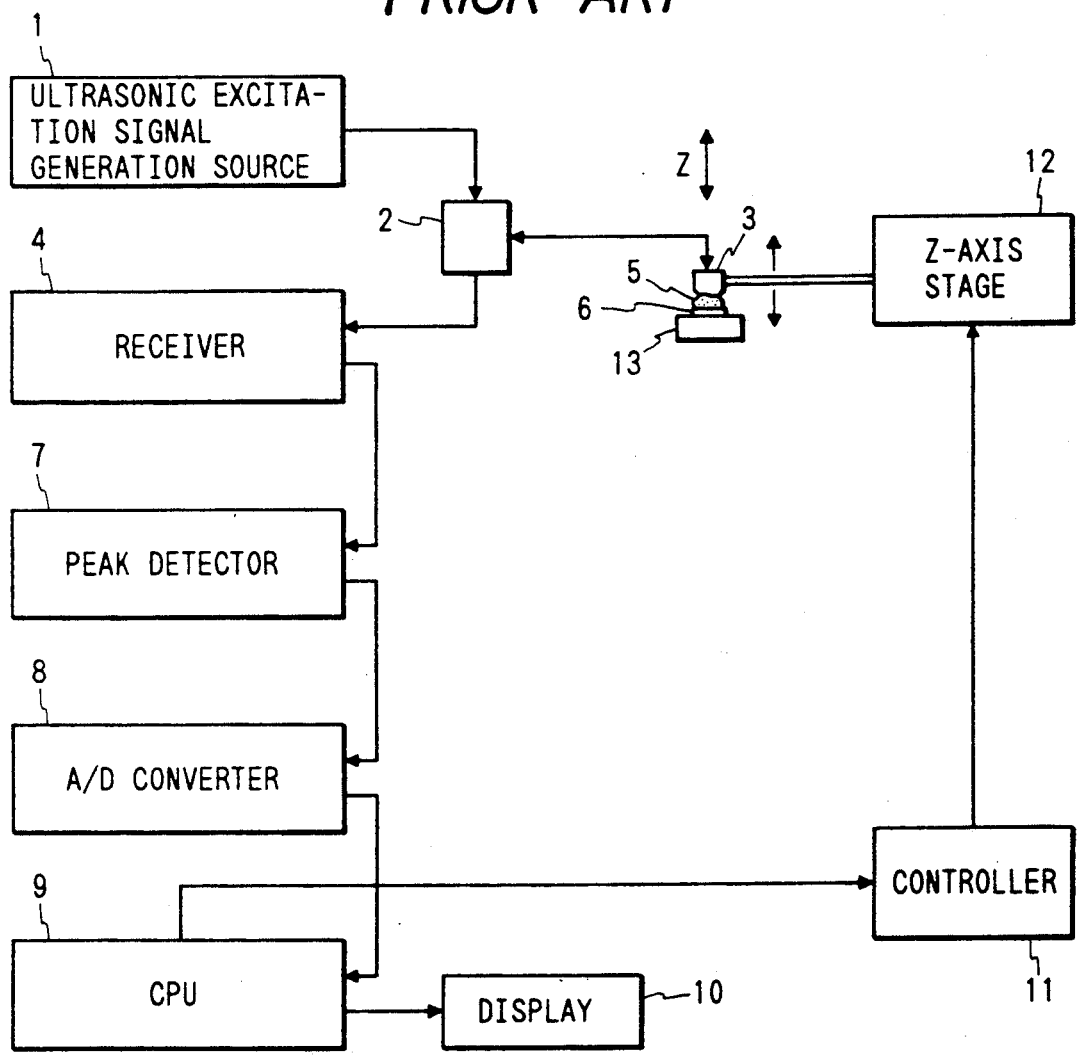
FIG. 2 is a schematic view showing a conventional acoustic microscope system.
Figure 3A:
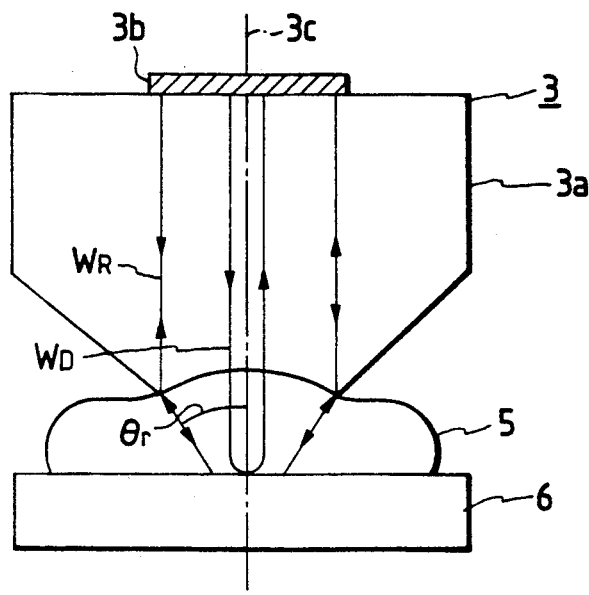
FIG. 3A is an enlarged sectional view showing the conventional acoustic probe.
Figure 3B:
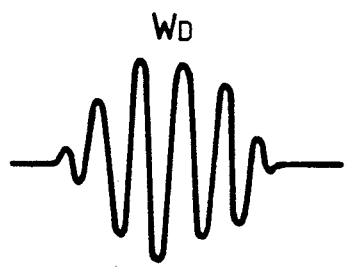
FIGS. 3B to 3E show waveforms detected by the conventional acoustic probe.
Figure 3C:
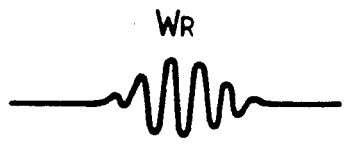
Figure 3D:
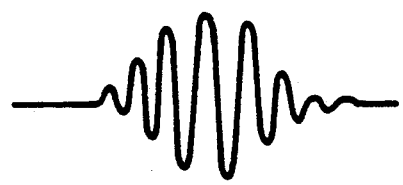
Figure 3E:
Figure 4:
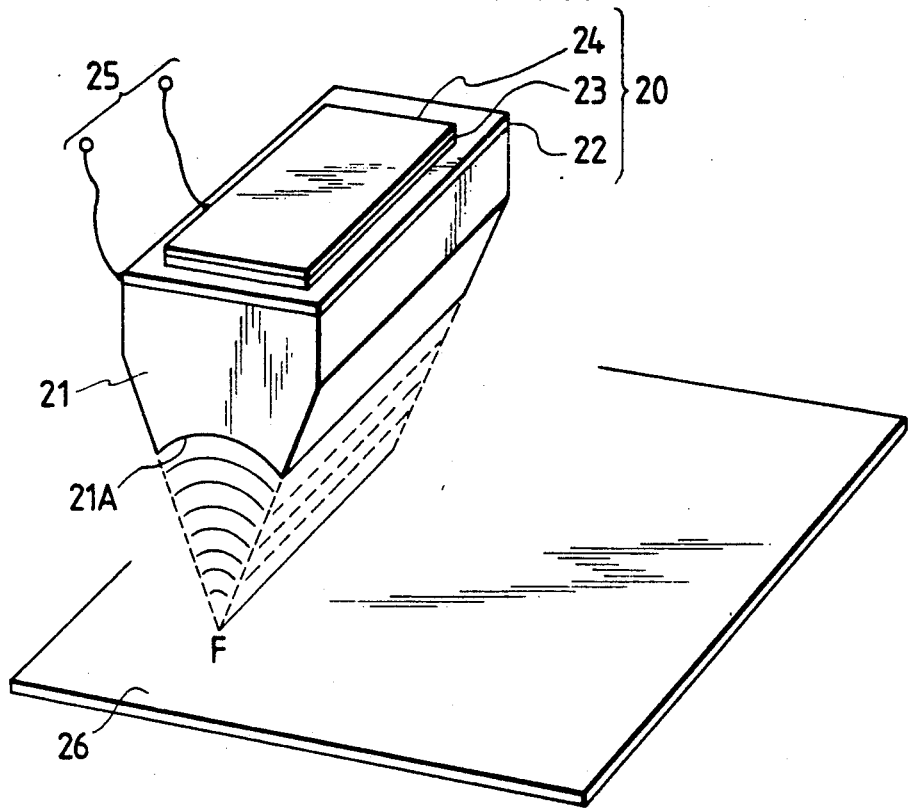
FIG. 4 shows a conventional acoustic probe of the line-focus-beam type.
Figure 5:
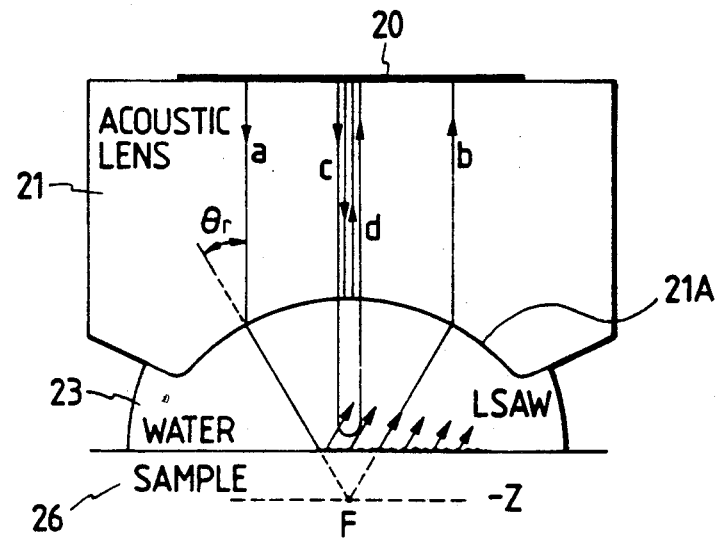
FIG. 5 is a sectional view of the conventional acoustic probe shown in FIG. 4.

FIG. 6A is a schematic view showing a layout of an acoustic microscope system according to the first embodiment of the present invention. The fundamental devices and arrangement thereof of this system are essentially the same as that of the conventional system shown in FIG. 2 except that an improved ultrasonic probe 14, an attenuator 30 and a switch 18 are provided and, the central processing unit (CPU) 9 performs different jobs and calculations, an attenuator 30 and a switch $SW_A$ being provided for appropriately selecting the attenuator, as described hereinbelow. A description of identical elements is omitted.

Figure 7A:
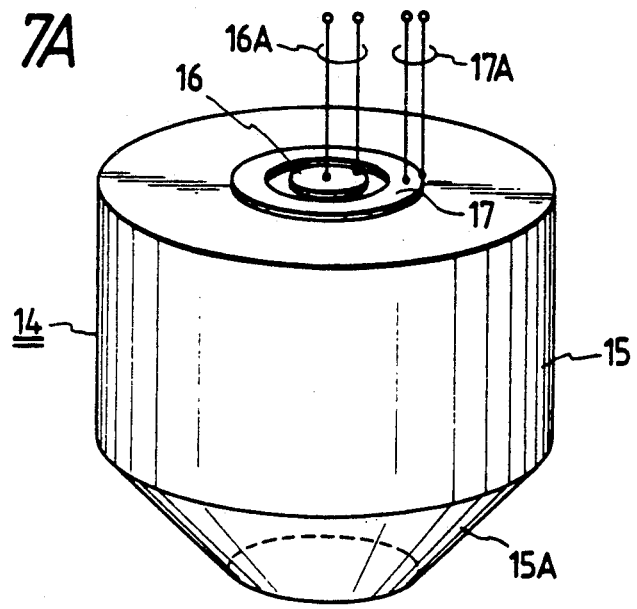
FIG. 7A is a perspective view showing an acoustic probe of the point-focus-beam type according to the first embodiment of the invention shown in FIG. 6A.
Figure 7B:
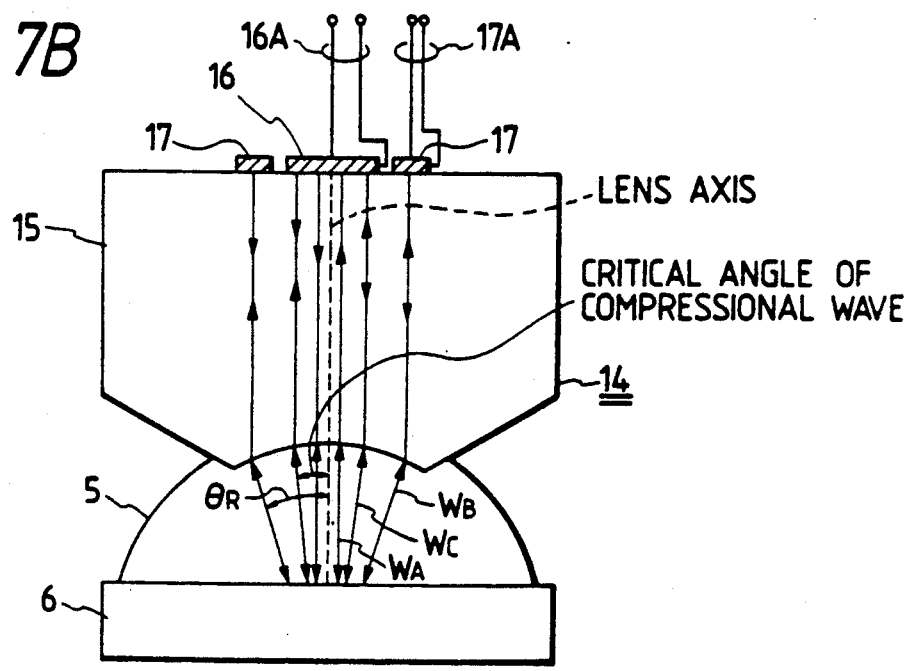
FIG. 7B is a sectional view showing the acoustic probe of the first embodiment of the invention shown in FIG. 6A.

As shown in FIGS. 7A and 7B, the ultrasonic probe 14 according to the first embodiment of the present invention is provided with a first circular ultrasonic transducer 16, a second annular ultrasonic transducer 17 having an inside diameter that is greater than the diameter of the first transducer 16, and an acoustic lens 15 of the point-focus-beam type.

The switch 18 performs selection between terminals 18a and 18b in response to a command supplied from the CPU 9. When the terminal 18a is selected, the first drive mode is activated and a high-frequency burst signal generated by the ultrasonic excitation source 1 is supplied only to the first ultrasonic transducer 16. When the terminal 18b is selected, on the other hand, the second drive mode is activated and the high-frequency burst signal is supplied to both the first and second ultrasonic transducers 16 and 17 simultaneously. Selection between the terminals 18a and 18b in the switch 18 may be performed manually other than by the CPU 9.

FIG. 7A is a perspective view showing an enlarged probe 14 employed in the first embodiment under consideration, and FIG. 7B is a sectional view illustrating how ultrasonic waves radiate or reflect. As shown in FIG. 7A, the probe 14 has the cylindrical acoustic lens 15 with a frustoconical distal end 15A. The first circular ultrasonic transducer 16 is disposed on the cylindrical cross section of the acoustic lens at its back side in combination with the second annular ultrasonic transducer 17 having an inner diameter that is greater than the outer diameter of the first transducer 16. External lead wires 16A and 17A connect to the positive and negative electrodes for each transducer. The frustoconical end 15A has a concave trip from which to radiate ultrasonic waves.

The diameter of the first circular ultrasonic transducer 16 is of a size that permits an ultrasonic wave to be incident within the critical angle for the compressional wave (or an angle in its neighborhood), or of such a size that the ultrasonic wave admitted within said critical angle (or an angle in its neighborhood) propagates through the surface of the sample material and that the irradiated leaky surface skimming compressional wave (LSSCW) component is received again by the first transducer.

The inside and outside diameters of the second annular ultrasonic transducer 17 are of sizes that permit an ultrasonic wave to be incident within the critical Rayleigh angle (or an angle in its neighborhood), or of such sizes that the ultrasonic wave admitted within the critical angle (or an angle in its neighborhood) propagates through the surface of the testpiece as a leaky surface acoustic wave (Rayleigh wave) and that an irradiated transversal leaky surface acoustic wave is received again by the transducer.

The angle of incidence of ultrasonic waves and the angle at which the leaky waves irradiate are symmetrical with respect to the axis of the acoustic lens and are equal to each other. This phenomenon holds true not only with the critical angle for the compressional wave (or an angle in its neighborhood) but also with the critical Rayleigh angle (or an angle in its neighborhood).

Transmission and reception of ultrasonic waves are described below with reference to FIG. 7B.

(1) First Drive Mode (With Terminal 18a Selected)

When the terminal 18a is selected, the high-frequency burst signal generated by the ultrasonic excitation source 1 is supplied only to the first ultrasonic transducer 16. In response to this signal, the first transducer 16 radiates ultrasonic waves as indicated by arrows in FIG. 7B, causing the following two kinds of reflected wave: a vertical reflection wave $W_A$ reflected directly from the testpiece 6; a leaky surface skimming compressional wave $W_C$ (irradiating at the same angle as the incident angle) that irradiates from the surface of the testpiece 6 after having skimmed it. That is, the first ultrasonic transducer 16 receives not only the vertical reflection wave $W_A$ but also the leaky surface skimming compressional wave $W_C$ irradiated from the testpiece 6. Therefore, these two waves $W_A$ and $W_C$ interfere with each other at the first transducer 16 and the composite wave is passed through the directional coupler 2 to be sent to the receiver 4 for signal reception.

Figure 8A:
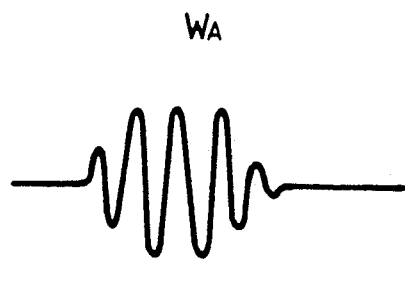
FIGS. 8A to 8D show waveforms detected by the acoustic microscope system according to the first embodiment of the invention.
Figure 8B:
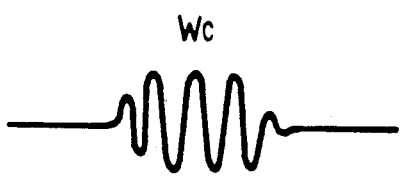
Figure 8C:
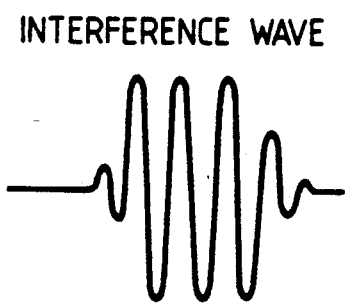
Figure 8D:
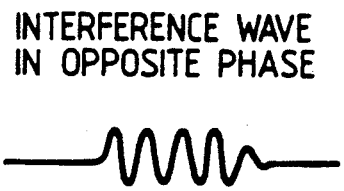

FIGS. 8A to 8D show the waveforms of various waves that are produced in the case described above. FIG. 8A depicts the vertical reflection wave $W_A$, FIG. 8B depicts the leaky surface skimming compressional wave $W_C$, FIG. 8C depicts the wave of interference between in-phase components, and FIG. 8D, the wave of interference between 180° out-of-phase components.

Figure 1:
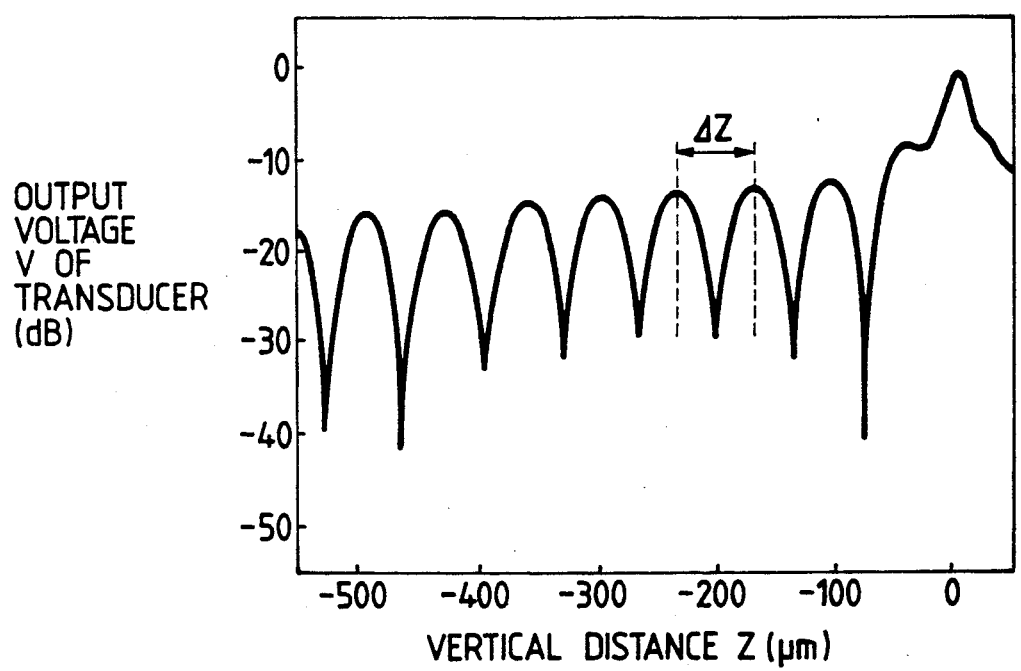
FIG. 1 is a graph showing an example of general V(z) curve.

The interference waves described above are obtained at each position of sampling by the Z-axis stage 12, producing a V(z) curve that differs in shape from the curve shown in FIG. 1 but which is characterized by the same parameters. The V(z) curve can be constructed by operations in the CPU 9, and the curve is appropriately displayed on the display device 10.

(2) Second Drive Mode (With Terminal 18b Selected)

When terminal 18b is selected, the high-frequency burst signal generated by the ultrasonic excitation source 1 is supplied to both the first and second transducers 16 and 17 thereby driving the two transducers simultaneously. As a result, the two transducers radiate ultrasonic waves as illustrated by arrows in FIG. 7B.

As shown in FIG. 7B, the ultrasonic wave radiated from the first transducer 16 is directly reflected by the testpiece 6 and received by the transducer 16 itself as the vertical reflection wave $W_A$. The ultrasonic wave radiating from the second transducer 17 is admitted into the couplant 5 at larger than the critical angle for the compressional wave and substantially within the critical Rayleigh angle $\theta_r$ (the angle of incidence at the concave lens surface of the acoustic lens 15) and propagates through the surface of the testpiece 6 as a transversal leaky surface acoustic wave LSAW and irradiates from the surface to the transducer as indicated by $W_B$, whereupon the component that is irradiated from the testpiece at the position symmetrical to the incident position with respect to the axis of the acoustic lens is received by the second transducer 17. These two waves $W_A$ and $W_B$ interfere with each other to produce a composite wave that is passed through switch 18 and directional coupler 2 to be sent to the receiver 4.

The Z-axis stage 12 (FIG. 6A) is operated to move the probe 14 along the Z-axis (in the vertical direction) for each sampling point. At each sampling point, the terminal 18b is selected to produce the wave of interference between the vertical reflection wave $W_A$ and the irradiated leaky surface acoustic wave $W_B$. The resulting interference waves are received by the receiver 4, have their peak detected by the peak detector 7 and taken into the CPU 9 for constructing a V(z) curve of the kind similar to that shown in FIG. 1.

While different V(z) curves are constructed by selecting the first and second drive modes, the acoustic velocity of the leaky surface skimming compressional wave can be calculated on the basis of the V(z) curve for the first mode and, independently, the acoustic velocity of the leaky elastic surface (Rayleigh) wave can be calculated from the V(z) curve for the second mode. In either case, the CPU 9 performs the necessary computations automatically.

Needless to say, various physical properties such as the elastic characteristics of the material of the testpiece to be analyzed can be estimated from the thus calculated values of two acoustic velocities. Now supposing the velocity of the leaky surface skimming compressional wave (LSSCW) is represented by $C_1$, the following equations (2) and (3) are expressed as follows:

$$C_1 = \sqrt{\frac{E}{\rho} \cdot \frac{1 - \nu}{(1 + \nu)(1 - 2\nu)}} \quad (2)$$

$$C_R = \frac{0.875 + 1.125\nu}{1 + \nu} \sqrt{\frac{E}{\rho} \cdot \frac{1}{2(1 + \nu)}} \quad (3)$$

where E represents Young'2 Modulus, $\nu$ represents Poisson's ratio, and $\rho$ represents density.

Figure 9A:
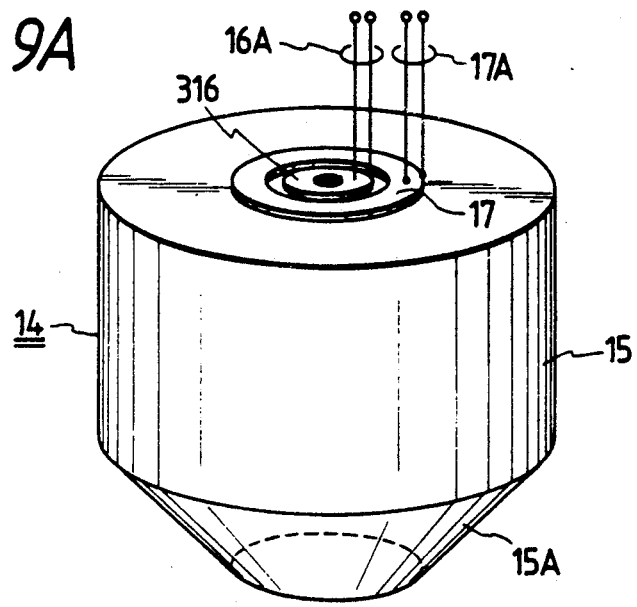
FIG. 9A is a perspective view showing one arrangement of an acoustic probe according to the first embodiment of the invention.
Figure 9B:
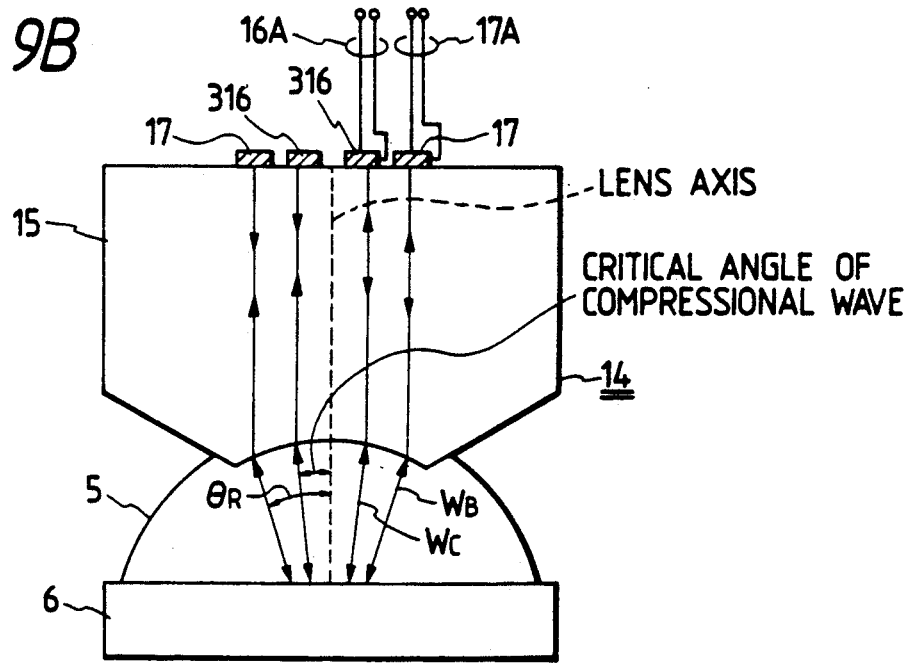
FIG. 9B is a sectional view of the arrangement shown in FIG. 9A.

According to the first embodiment of the invention, the first transducer 16 receives both the vertical reflection wave $W_A$ and the leaky surface skimming compressional wave $W_C$ irradiated from the surface of the testpiece. However, the invention is not limited thereto or thereby. As shown in FIGS. 9A and 9B, for example, the acoustic probe 14 may be provided with an annular first transducer 316 which receives only the irradiated leaky surface skimming compressional wave $W_C$. In this case, the receiver 4 receives the signal supplied from the transducer and a signal from the ultrasonic excitation source 1 through an attenuator 30 which signal having a frequency equal to that of the high-frequency burst signal supplied to the transducer, thereby electrically interfering with each other and producing an analog electric composite signal. The composite signal is applied to the peak detecting device 7 and the peaks of the composite signal are detected.

Further, the acoustic microscope system may employ more than two transducers which are selectively actuated thereby applying to various kinds of testpieces having different velocity, for example, to be analyzed or the mode of measurement that is appropriate for the specific material.

Furthermore, although both the first and second transducers 16 and 17 are actuated in the second drive mode according to the first embodiment as described above, the invention is not limited thereto or thereby. For example, only the second transducer 17 may be actuated in the second drive mode in which the switch 18b is selected.

Moreover, an acoustic matching layer may appropriately be provided between the acoustic lens and the couplant.

FIGS. 6B, 6C and 6D illustrate conditions of possible switch types of the switch 18 shown in FIG. 6A.

FIG. 6B is a switch type for two annular transducers with an arrangement corresponding to the arrangement of the first embodiment as shown in FIGS. 9A and 9B. In this arrangement, an inner transducer receives the irradiated leaky surface skimming compressional wave and an outer transducer receives the irradiated leaky surface acoustic wave, and a switch $18_1$ selects one of the two annular transducers while a switch $SW_A$ for actuating an attenuator 30 is turned on, thereby supplying to the receiver 4 an electric signal having a frequency equal to that of the ultrasonic wave excitation signal generated by the source 1, so that the signal returning from the testpiece 6 electrically interferes with the signal at the receiver 4 before being supplied to the peak detector 7.

FIG. 6C shows another type of the switch for one circular transducer disposed at the center of the acoustic lens 14 and two annular transducers disposed so as to surround the circular transducer. In this arrangement, a switch $18_2$ always actuates the circular transducer while selecting one of the two annular transducers. The switch $SW_A$ is always turned off. This switch operates in the same manner as the switch shown in FIG. 6B. However, the circular transducer is used for generating a vertical interference wave (reference wave) and not the ultrasonic excitation signal generation source 1.

FIG. 6D shows another type of switch for a transducer arrangement in which there is a circular transducer at the center of the acoustic lens and one annular transducer which arrangement is identical to the arrangement shown in FIGS. 7A and 7B. In this arrangement, a switch $18_3$ always actuates the circular transducer and turns on or off the annular transducer while the switch $SW_A$ is always turned off. Thus, the switch shown in FIG. 6D operates similarly to the switch 18 shown in FIG. 6A and as described with respect to FIGS. 7A and 7B.

The type of switch 18 may appropriately be selected in accordance with the arrangement of the transducer.

A second embodiment of the invention will now be described in detail with reference to the accompanying FIGS. 10-12.

Figure 10:
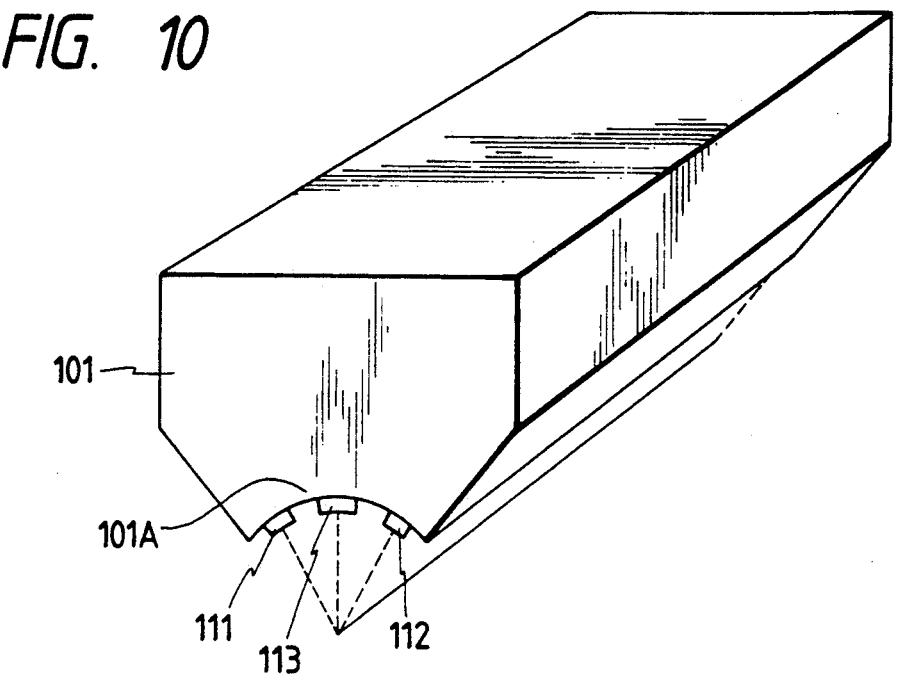
FIG. 10 is a perspective view showing an acoustic probe of the line-focus-beam type according to the second embodiment of the present invention.

FIG. 10 is a perspective view showing an ultrasonic probe of the line-focus-beam type according to the second embodiment of the present invention. In this embodiment, three strip-shaped ultrasonic transducers 111, 112 and 113 are provided on a cylindrical lens surface 101A of an acoustic lens 101 of the probe. The three transducers 111, 112 and 113 are formed along the longitudinal direction of the cylindrical lens surface 101A. The ultrasonic beams radiating from the three transducers mounted on the lens surface will converge at focal points F (see FIG. 11), thus forming a linear focus beam.

Figure 11:
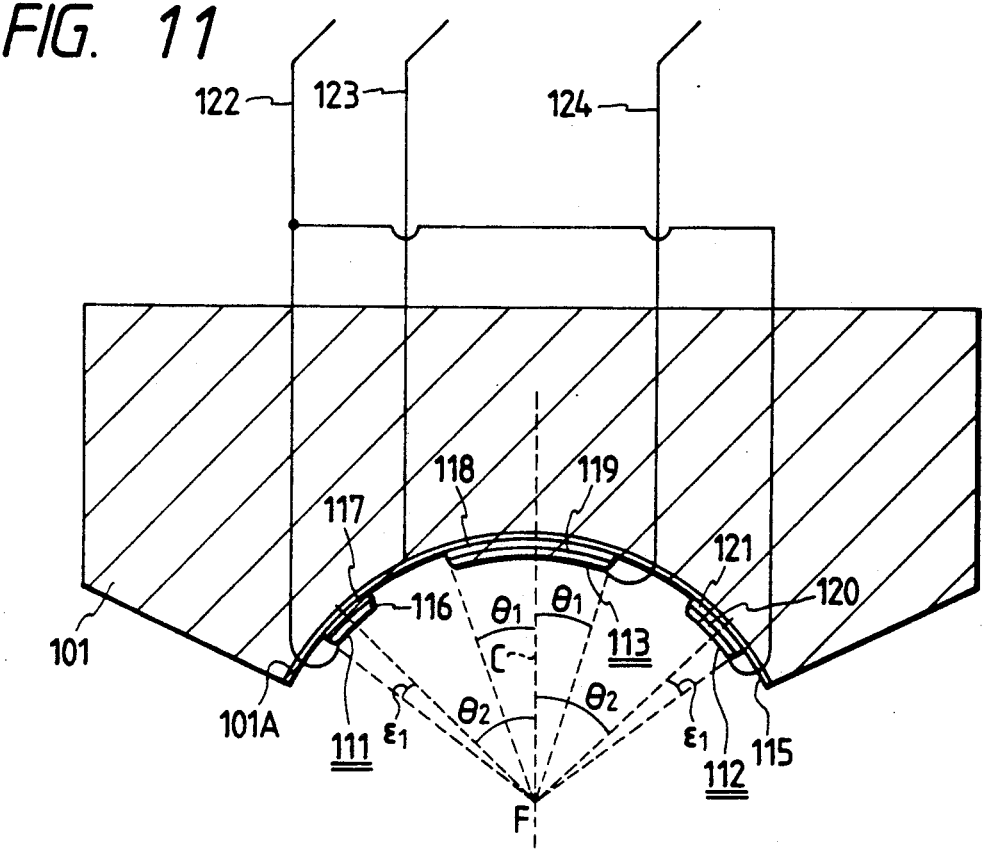
FIG. 11 is a sectional view of the acoustic probe shown in FIG. 10.

FIG. 11 is a cross sectional view illustrating the ultrasonic probe according to the second embodiment under discussion. A lower electrode 115 is mounted on the acoustic lens surface 101A and, on the electrode 115 are piezoelectric elements formed of ZnO or the like 117, 119 and 121 as well as upper electrodes 116, 118 and 120 disposed on the piezoelectric elements 117, 119 and 121, respectively, in different positions thereby forming the transducers 111, 113 and 112, respectively.

The transducer 113 is formed on the central axis C of the lens surface 101A in such a way that its center is in alignment with the central axis C. The incident (or reflection) angle $\theta_1$ for the transducer 113 is adjusted to a maximum incident angle that is slightly greater than the critical angle for compressional wave. Hence, the position of the end of the transducer 113 (or more correctly, the position of the end of the piezoelectric element 119) is determined in such a way as to provide the above-defined angle of incidence.

Transducers 111 and 112 are formed in positions on the lens surface 101A that are symmetric to each other with respect to the central axis C. The angle $\theta_2$, as defined with respect to the center of each transducer 111 or 112, formed with the center line C is set to the critical Rayleigh angle (or a value in its neighborhood). The far end of each transducer 111 or 112 is positioned in such a way as to provide an incident angle equal to $\theta_2 + \epsilon_1$, where $\epsilon_1$ is an angle of margin sufficient for a certain wave to be admitted and reflected as the leaky elastic surface (Rayleigh) wave LSAW.

Figure 12:
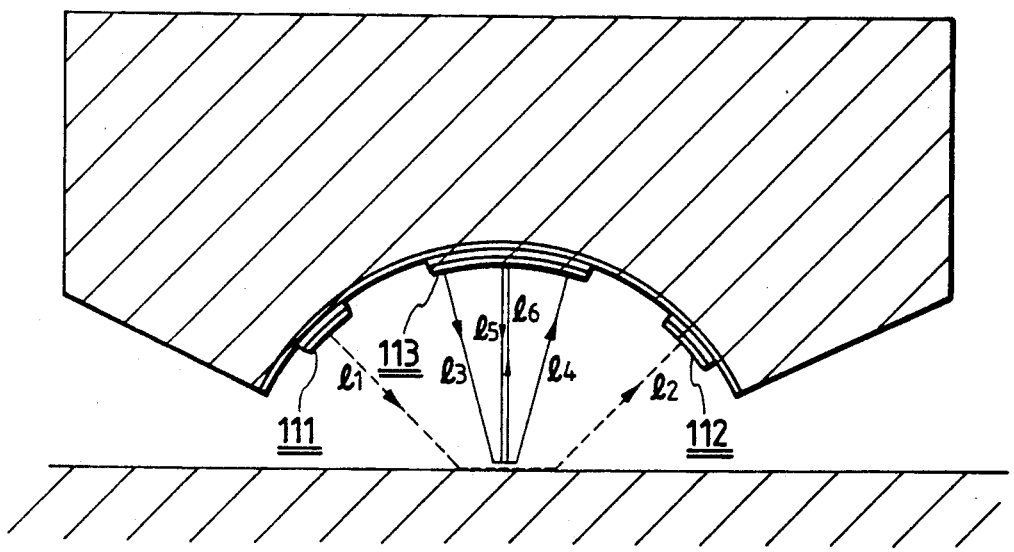
FIG. 12 is a sectional view of the acoustic probe shown in FIG. 10 illustrating incident and reflecting waves.

FIG. 12 shows how ultrasonic waves radiate are reflected back to the transducers 111, 112 and 113. The ultrasonic wave radiated from the transducer 111 along the path $l_1$ propagates through the surface of a testpiece 130 as a leaky surface acoustic wave (LSAW) $l_{12}$ and is irradiated as the Rayleigh wave that is admitted into the transducer 112 by travelling the path $l_2$. The center transducer 113 radiates straight-down an ultrasonic wave along the path $l_5$ and it is vertically reflected back to the same transducer 113 by travelling along the path $l_6$. At the same time, the center transducer 113 radiates an ultrasonic wave that is incident on the surface of he testpiece 130 substantially within the critical angle for the compressional wave along the path $l_3$ and which propagates on the surface of the testpiece 130 as a leaky surface skimming compressional wave (LSSCW) and irradiates from the surface of the testpiece 130 to travel toward the center transducer 113 along the path $l_4$.

The three reflecting and irradiating waves which travel along $l_2$, $l_4$ and $l_6$ interfere with each other to form a composite wave employed for constructing the V(z) curve.

As shown in FIG. 11, a common lead wire 123 connects to the lower electrode 115, whereas a common lead wire 122 connects to the upper electrodes 116 and 120 and a lead wire 124 connects to the upper electrode 118. Because of this electrical connection, the transducers 111 and 112 can be driven by a common wiring consisting of the leads 122 and 123, and the transducer 113 can be driven by the leads 124 and 123.

If one wants to determine the velocity of the Rayleigh wave for a material of interest, he may apply a voltage pulse both to leads 122 and 123 and to leads 124 and 123, whereupon a signal due to the Rayleigh wave (leaky surface acoustic wave) LSAW is received at leads 122 and 123 and a signal due to the vertical reflection wave is obtained at leads 124 and 123. By adding the two signals electrically, a signal for the interference wave and, hence, a signal for the V(z) curve can be obtained. If desired, leads 122 and 124 may be replaced by a single common wire and in this case, too, the intended signal for interference wave can be obtained.

If one wants to determine the velocity of the leaky surface skimming compressional wave for the testpiece, he may apply a voltage pulse only to leads 124 and 123, whereupon a signal for the V(z) curve of the compressional wave including a vertical reflection wave component and leaky surface skimming compressional wave (LSSCW) component can be obtained.

In the second embodiment described above, three ultrasonic transducers are provided in selective positions on the acoustic lens surface, so the reception of unwanted reflected waves can be prevented to insure the construction of an accurate V(z) curve. Further, there is no need to make the acoustic lens 101 from sapphire which is expensive and difficult to machine or work and this enables the lens to be fabricated in an easy and inexpensive way using plastc resin such as PMMA or the like. Another advantage of the invention is that the acoustic velocity of the compressional wave can be measured without any effects of the transversal (Rayleigh) wave.

In the second embodiment, on the other hand, the angle of incidence $\theta_1$ is set to a maximum incident angle that is slightly greater than the critical angle for the compressional wave. It should, however, be noted that if somewhat lower precision of measurements is permitted, the angle of incidence $\theta_1$ may be somewhat smaller than the critical angle for the compressional wave (i.e., an angle in its neighborhood).

Furthermore, in the second embodiment, the central transducer 119 is formed of a single strip-like transducer for receiving the vertical reflection wave and the leaky surface skimming compressional wave. However, the invention is not limited thereto or thereby. For example, as arranged in the first embodiment, the transducer 119 may consist of a pair of strip-like transducers for receiving merely the leaky surface skimming compressional wave irradiating from the surface of the testpiece. In this case, another transducer mounted on the center of the acoustic lens for receiving merely the vertical reflection wave may additionally be provided.

In any event, according to the second embodiment of the invention described above in detail, no acoustic matching layer is required to be disposed between the ultrasonic probe and the couplant.

A third embodiment of the invention will now be described in detail with reference to accompanying FIGS. 13 and 14.

Figure 13:
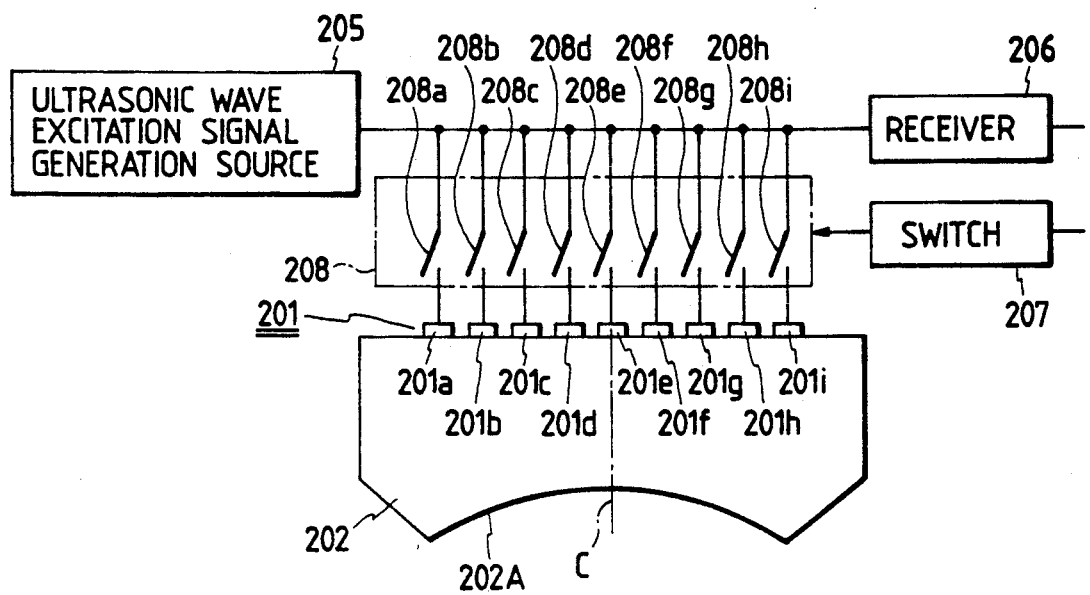
FIG. 13 is a schematic sectional view of an acoustic probe according to the third embodiment of the invention.

FIG. 13 is a view showing a line-focus-beam probe according to the third embodiment of the present invention. FIG. 14 is a top view of one example of an arrangement of the transducer elements provided on that ultrasonic probe. As shown, the probe consists of a transducer 201 and an acoustic lens 202. The acoustic lens 202 has a cylindrical concave lens surface 202A on bottom surface, with the transducer 201 being coupled to the opposite (top) side. The concave lens surface 202A has a longitudinal axis directing perpendicular to the paper of FIG. 13. The transducer 201 is composed of nine transducing elements 201a–201i, with four (201a–201d, or 201f–201i) being positioned on either side of the central axis C of the lens and one element (201e) being positioned on the central axis C. This arrangement of nine transducing elements is just one example and is in no way to be taken as limiting as well as that of the other embodiments of the present invention described above.

Figure 14:
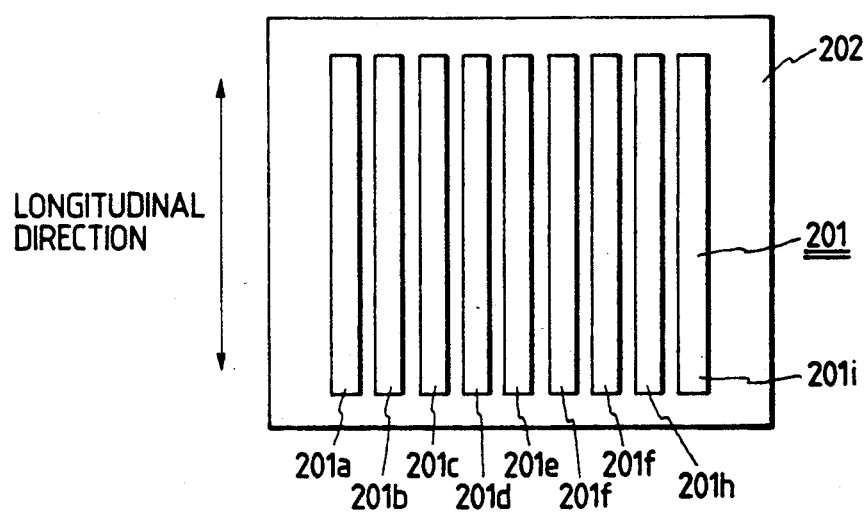
FIG. 14 is a top view showing a transducer of the acoustic probe embodying the third embodiment shown in FIG. 13.

As shown in FIG. 14, the transducing elements 201a–201i are elongated strips that are arranged parallel to the longitudinal axis of the cylindrical concave portion of the acoustic lens 202. Needless to say, each transducing element consists of a piezoelectric element and a pair of upper and lower electrodes.

The transducing elements 201a–201i are connected to an external ultrasonic excitation source 205 such as an impulse generator or a tone burst generator and a receiver 206 via a switch 208 which is subject to ON/OFF control by a switching circuit 207. The ultrasonic excitation source 205 is a power source for exciting ultrasonic waves and it may generate either pulsed waves or burst waves. The receiver 206 receives signals for reflected and irradiated waves returning from a testpiece to be analyzed.

The switching circuit 207 selects and controls appropriate switching elements from among 208a–208i in the switch 208 in accordance with the testpiece to be analyzed. Take, for example, the case where the critical Rayleigh angle is the angle of incidence of a radiation from the transducing element 201b; then, the circuit 207 turns on the switching element 208b in order to select the transducing element 201b as an ultrasonic wave radiating device and, at the same time, the circuit 207 turns on the switching element 208h in order to select the oscillating element 201h as a device for receiving a leaky surface skimming compressional wave. Further, the circuit 207 turns on the switching element 208e as a device for radiating and receiving a vertical wave. The other switching elements remain off.

As a result, the excitation voltage from the transmitter 205 is applied to the transducing element 201b via switching element 208b, whereupon an ultrasonic wave is radiated at an angle equivalent to the critical Rayleigh angle of the testpiece. At the same time, a leaky surface acoustic wave (LSAW) develops on the surface of the testpiece and it is picked up by the transducing element 201h, whereas the transducing element 201e is selected by the turning-on of the switching element 208e, whereby the transducing element 201e radiates an incident vertical wave and receives a vertical reflection wave. The signals for the reflected waves picked up by the transducing elements 208e and 208h interfere with each other to form a composite signal that is received by the receiver 6 to provide data for constructing a V(z) curve.

The decision of which of the switching elements 208a–208i should be turned on depends on the testpiece to be analyzed or the mode of measurement that is appropriate for the specific testpiece. To name a few possible combinations, 208a and 208i may be turned on, or 208a and 208b and 208h and 208i may be turned on.

In the third embodiment described above, the transducing element 201e is turned on for generating an interference wave. Alternatively, this element may be kept off and a preliminarily generated equivalent of the signal for reflected wave, for example, an electric reference wave, may be added to the wave components picked up by the transducing elements that were turned on.

In the case where one only need detect the V(z) curve of the surface wave that is generated substantially at the critical angle for the compressional wave, turning on the transducing element 201e will suffice if it covers the range of incident angles up to the critical angle for the compressional wave. Otherwise, those transducing elements which permit optimum incident angles, say 201d and 201f, may be turned on in addition to 201e.

The line-focus-beam and point-focus-beam probes have their own merits and drawbacks. For instance, C-scan measurements are possible with the point-focus-beam type they are impossible with the line-focus-beam type. In anisotropic measurements, the line-focus-beam type insures a higher precision than the point-focus type. Further, the point-focus type is not suitable for application to high-attenuation materials. On the other hand, since the propagating ultrasonic waves contain not only those of the intended direction but also those of the unwanted additional directions, the point-focus-beam type provides lower precision of anisotropic measurement than does the line-focus-beam type.

Under the circumstances, the choice of the point-focus-beam type or the line-focus-beam type depends upon the object of a particular measurement or its method (the two factors may collectively be referred to as the "mode of measurement").

The ultrasonic excitation source and arrangement thereof, as described above, may be an impulse generator or a tone burst generator as in the conventional acoustic microscope system.

In accordance with the present invention, the leaky surface acoustic wave (Rayleigh wave) and the leaky surface skimming compressional wave can be received independently of each other by at least two separate ultrasonic transducers, and the acoustic velocities of those waves can be individually determined from the corresponding V(z) curves. Therefore, it becomes possible to detect and measure the elastic characteristics of a material much accurately.

Further, according to the, present invention, the ultrasonic probe is constructed so as to avoid receiving unwanted reflected waves and this enables the construction of a precise V(z) curve.

Furthermore, the acoustic lens of the probe can be fabricated from an inexpensive material such as a plastic material like PMMA or the like in an easy manner without necessitating an acoustic matching layer between the acoustic lens and couplant.

On the other hand, the critical Rayleigh angle for the line-focus-beam probe is inherent in the testpiece to be analyzed and no surface wave will be excited even if an ultrasonic wave is admitted into the testpiece at angles smaller than the critical Rayleigh angle. At the same time, if the incident angle is greater than the critical value, a surface wave other than the Rayleigh wave may be activated, and the precision of measurement of sound velocity may deteriorate. It has, therefore, been necessary to use several probes that permit ultrasonic waves to be incident at optimum angles in accordance with the specific testpiece to be analyzed. When there is a change in testpiece, the probe must have also been changed or the tilting of the testpiece must have been adjusted, thereby requiring extra time and labor before the actual measurement starts.

However, according to the present invention, a single probe can realize various modes of measurements by merely permitting a plurality of transducing strips to be selectively turned on. This offers great benefits in practical applications since the preliminary adjustments of the probe can be simplified and the switch may be selectively activated instead of exchanging a plurality of probes when a different type of testpiece is to be analyzed.

What is claimed is:

1. An acoustic microscope system for evaluating a material utilizing a V(z) curve constructed in accordance with waves returning from the material while radiating ultrasonic waves toward the material, comprising:

a source means for generating an ultrasonic excitation signal;

an ultrasonic probe connected to said ultrasonic excitation signal generation source for converting said excitation signal into an ultrasonic wave and radiating said ultrasonic wave toward the material to be analyzed, said ultrasonic probe receiving waves returning from the material, said ultrasonic probe comprising:

an acoustic lens for focusing said ultrasonic wave;

a first transducing means provided on said acoustic lens for radiating said ultrasonic wave toward the material substantially within a critical angle for a compressional wave, said first transducing means receiving a leaky surface skimming compressional wave irradiating from the material; and a second transducing means provided on said acoustic lens independently of said first transducing means for radiating said ultrasonic wave toward the material at larger than the critical angle for the compressional wave and substantially within a critical Rayleigh angle, said second transducing means receiving a leaky surface acoustic wave irradiating from the material, a switching means disposed between said excitation signal generation source and said ultrasonic probe for selectively actuating said first and second transducing means;

means for moving said ultrasonic probe towards and away from the material; and means for constructing the V(z) curve in accordance with output signals from at least one of said first and second transducing means.

2. The acoustic microscope system of claim 1, wherein said first transducing means also receives a vertical reflection wave vertically reflected by the material to be analyzed, said vertical reflection wave interfering acoustically with said leaky surface skimming compressional wave, said first transducing means outputting an interference signal to be supplied to said V(z) curve construction means.

3. The acoustic microscope system of claim 1, wherein said first transducing means receives only said leaky surface skimming compressional wave.

4. The acoustic microscope system of claim 3, further comprising means for electrically interfering said leaky surface skimming compressional wave with a reference signal having a frequency equal to that of said ultrasonic excitation signal, said interfering means outputting an interference signal to said V(z) curve construction means.

5. The acoustic microscope system of claim 3, further comprising a third transducing means for receiving a vertical reflection wave reflected vertically by the material to be analyzed and performing as a reference signal, said reference signal being interfered electrically with an output signal of said first transducing means thereby forming an interference signal employed as a factor of the V(z) curve by said V(z) curve construction means.

6. The acoustic microscope system of claim 1, wherein said ultrasonic probe is of a point-focus-beam type.

7. The acoustic microscope system of claim 1, wherein said ultrasonic probe is of a line-focus-beam type.

8. The acoustic microscope system of claim 6, wherein said acoustic lens comprises a frustoconical distal end having a first circular surface and a second surface opposite said first surface on which a spherical concave lens portion is provided.

9. The acoustic microscope system of claim 7, wherein said acoustic lens is trapezoidal in cross section having a first flat surface and a second surface opposite said first surface on which a cylindrical concave lens portion is provided.

10. The acoustic microscope system of claim 6, wherein said first transducing means comprises a circular transducer, and said second transducing means comprises an annular transducer having an inner diameter larger than an outer diameter of said first transducer.

11. The acoustic microscope system of claim 6, wherein said first transducing means comprises an annular transducer, and said second transducing means comprises an annular transducer having an inner diameter larger than an outer diameter of said first transducer.

12. The acoustic microscope system of claim 7, wherein each of said first and said second transducing means comprises a strip-shaped transducer.

13. The acoustic microscope system of claim 7, wherein said first and second transducing means comprise a plurality of elongated, strip-shaped transducers which extend in a direction parallel to a longitudinal axis of said acoustic lens.

14. The acoustic microscope system of claim 1, wherein each of said first and second transducing means comprises a piezoelectric element and a pair of upper and lower electrodes provided on an upper and lower surface of said piezoelectric element.

15. The acoustic microscope system of claim 8 or 9, wherein said first and second transducing means are mounted on said first surface of said acoustic lens.

16. The acoustic microscope system of claim 8 or 9, wherein said first and second transducing means are mounted on said second surface of said acoustic lens.

17. The acoustic microscope system of claim 15, wherein said acoustic lens is formed of sapphire.

18. The acoustic microscope system of claim 15, wherein said acoustic lens is formed of a plastic material (PMMA).

19. The acoustic microscope system of claim 2, wherein said V(z) curve constructing means comprises:
means for receiving output signals of said ultrasonic probe;
means for detecting a peak value of the signals supplied from said receiving means, said peak value detecting means outputting an analog signal;
means for converting said analog output signal of said peak value detecting means into digital form;
a control means for calculating said digital output signal of said A/D converting means thereby describing the V(z) curve, said control means controlling said ultrasonic probe moving means and said switching means; and
means for displaying the V(z) curve.

20. The acoustic microscope system of claim 3, wherein said V(z) curve constructing means comprises:
an attenuator connected to said source means;
means for receiving an attenuated signal from said attenuator and for receiving output signals of said ultrasonic probe, said attenuated signal and said output signals electrically interfering with each other, said receiving means thereby outputting an analog composite signal;
means for detecting a peak value of said composite signal output by said receiving means, said peak value detecting means outputting an analog peak value signal;
means for converting said analog peak value signal and said analog composite signal into digital form and for supplying said digital peak value signal and said digital composite signal to the V(z) curve constructing means;
a control means for controlling said ultrasonic probe moving means and said switching means; and
means for displaying the V(z) curve.

21. The acoustic microscope system of claim 1, wherein said switching means switches between a first position at which only said first transducing means is actuated and a second position at which said first and second transducing means are actuated.

22. The acoustic microscope system of claim 1, wherein said switching means switches between a first position at which only said first transducing means is actuated and a second position at which only said second transducing means is actuated.

23. An acoustic microscope system for evaluating a material utilizing a V(z) curve obtained from waves returning from the material while radiating an ultrasonic wave toward the material, comprising:
means for generating an ultrasonic excitation signal;
an ultrasonic probe connected to said ultrasonic excitation signal generating means for converting said ultrasonic excitation signal into an ultrasonic wave and radiating said ultrasonic wave toward the material, said ultrasonic probe receiving waves returning from the material, said ultrasonic probe comprising:
an acoustic lens for focusing said ultrasonic wave; and
transducing means, provided on said acoustic lens, for radiating said ultrasonic wave toward the material and for receiving a leaky surface skimming compressional wave irradiating from the material and a leaky surface acoustic wave irradiating from the material, separately from said leaky surface skimming compressional wave;
means for moving said ultrasonic probe towards and away from the material;
means for constructing the V(z) curve in accordance with at least one of said leaky surface skimming compressional wave and said leaky surface acoustic wave received by said transducing means.

24. An ultrasonic probe for use in an acoustic microscope system for evaluating a material utilizing a V(z) curve obtained from a vertically reflected wave and leaky waves returning from the material by irradiating an ultrasonic wave toward the material, comprising:
an acoustic lens for focusing said ultrasonic wave;
a first transducing means provided on said acoustic lens for radiating said ultrasonic wave toward the material substantially within a critical angle for a compressional wave, said first transducing means receiving a leaky surface skimming compressional wave irradiating from the material; and a second transducing means provided on said acoustic lens independently of said first transducing means for radiating said ultrasonic wave toward the material at larger than the critical angle for said compressional wave and substantially within a critical Rayleigh angle, said second transducing means receiving a leaky surface acoustic wave irradiating from the material, wherein said first and second transducing means are selectively actuated.

* * * * *